United States Patent [19]

Wallau et al.

[11] Patent Number: 5,273,737

[45] Date of Patent: Dec. 28, 1993

[54] METHOD FOR THE PREPARATION OF CRYSTALLINE GALLOSILICATES, AND THEIR USE FOR THE PREPARATION OF CATALYSTS AND ADSORBENTS

[75] Inventors: Martin Wallau, Mainz; Rudolf Spichtinger, Frankfurt; Arno Tissler, Bonn; Klaus K. Unger, Bensheim; Roland Thome, Bonn, all of Fed. Rep. of Germany

[73] Assignees: Vaw Aluminum AG, Bonn; Veba Oel AG, Gelsenkirchen, both of Fed. Rep. of Germany

[21] Appl. No.: 725,036

[22] Filed: Jul. 3, 1991

[30] Foreign Application Priority Data

Jul. 3, 1990 [DE] Fed. Rep. of Germany ....... 4021118

[51] Int. Cl.$^5$ .................. C01B 33/24; C01F 7/00; B01J 29/04
[52] U.S. Cl. .................. 423/709; 423/710; 502/61
[58] Field of Search .................. 502/61; 423/709, 710, 423/707

[56] References Cited

U.S. PATENT DOCUMENTS

| | | | |
|---|---|---|---|
| 3,808,326 | 4/1974 | McDaniel et al. | 423/709 |
| 4,166,099 | 8/1979 | McDaniel et al. | 423/329 |
| 4,606,900 | 8/1986 | Kacirek et al. | 423/329 |
| 4,803,060 | 2/1989 | Occelli | 423/326 |
| 5,010,048 | 4/1991 | Petit et al. | 502/61 |
| 5,133,951 | 7/1992 | Occelli | 502/61 |
| 5,158,757 | 10/1992 | Deloprato et al. | 423/709 |

FOREIGN PATENT DOCUMENTS

| | | |
|---|---|---|
| 0094288 | 11/1983 | European Pat. Off. . |
| 0130013 | 1/1985 | European Pat. Off. . |
| 0150256 | 8/1985 | European Pat. Off. ............ 423/709 |
| 0323893 | 7/1989 | European Pat. Off. . |
| 0327189 | 8/1989 | European Pat. Off. . |
| 0443539 | 8/1991 | European Pat. Off. . |
| 1563559 | 4/1969 | France . |

OTHER PUBLICATIONS

"Kirk-Othmer Concise Encyclopedia of Chemical Technology" (1985) M. Grayson, Ed., John Wiley & Sons, Publisher, New York, pp. 772-774.
D. K. Simmons et al. (1987) *Journal of Catalysts*, vol. 106, pp. 287-291.
J. Ciric (1968) *Colloid Interface Sci*, vol. 28, pp. 315-324.

*Primary Examiner*—Carl F. Dees
*Attorney, Agent, or Firm*—Darby & Darby

[57] ABSTRACT

Disclosed is a method for preparing crystalline gallosilicates having a molar ratio of $SiO_2/Ga_2O_3 \geq 5$ an having a more uniform particle size with enhanced catalytic activity. According to the method of the invention, crystalline gallosilicates are prepared by adding an aged, gallosilicate nuclei-forming gel having a molar ratio of $SiO_2/Ga_2O_3 \geq 5$ to an aqueous, alkaline solution containing reactive silicon and gallium compounds to form a mixture. The mixture is then subjected to hydrothermal crystallization conditions to form the crystalline gallosilicate. The gallosilicates prepared by the disclosed method is useful for the preparation of catalysts and adsorbents and in processes for converting low molecular weight hydrocarbons to higher aliphatics and aromatic compounds.

24 Claims, No Drawings

METHOD FOR THE PREPARATION OF CRYSTALLINE GALLOSILICATES, AND THEIR USE FOR THE PREPARATION OF CATALYSTS AND ADSORBENTS

The present invention relates to a method for the preparation o& crystalline gallosilicates, particularly to gallosilicates analogous to zeolites, with a pentasil structure, and to their use for the preparation of catalysts and adsorbents. The chemical composition of the gallosilicates of the invention is described by the chemical formula $$(M^{n+})_{x/n}[(GaO_2)_x(SiO_2)_{96-x}]$$

wherein M represents an alkali or alkaline earth metal ions with a valency of n and x can assume values between 0 and 10.

BACKGROUND OF THE INVENTION

Gallosilicates are important catalysts in the petroleum and chemical industries for the preparation of valuable organic intermediates. Particularly noted for their dehydrating and aromatizing properties, gallosilicates have been employed for the conversion of lower molecular weight alkanes and alkenes to higher aliphatics and, in particular, one- and two-ring aromatic compounds. Aromatic compounds, such as benzene, toluene and xylene isomers, are important starting materials for the production of synthetic fibers, polyesters and other plastics as well as octane-increasing substances in lead-free motor gasolines.

Structurally, gallosilicates and other zeolites belong to the tectosilicates (see, for example, "Kirk-Othmer Concise Encyclopedia of Chemical Technology", M. Grayson, ed., John Wiley & Sons, publisher, New York, 1985, pages 772–774, for a review of zeolites). Their structure consists of $TO_4$ tetrahedra that are linked to each other by sharing of the oxygen atoms at the vertices. The nature of the T atoms is variable. Aside from the tetravalent silicon, trivalent atoms (such as aluminum or gallium) can be incorporated in the lattice framework. The tetrahedra form interlocking chains and layers and build up a defined interconnected system of channels and pores having opening widths of molecular dimensions. The opening widths of the channels and pores ultimately determine the accessibility to the inner cavity structure for materials of defined shape and form and thus confer molecular sieve-like properties to the porous bodies. Non-framework alkali or alkaline earth metal ions, present in zeolites after synthesis, readily undergo ion exchange with protons to produce effective, heterogeneous, acidic catalysts.

Methods for the synthesis of gallosilicates are described extensively in the technical and patent literature (see, for example, D. K. Simmons, J. Catal. 106: 287-291 (1987) and EP 0 130 013, published Feb. 1, 1985). In general, gallosilicates are prepared from aqueous, alkaline mixtures of reactive silicon dioxide and gallium(III) oxide by hydrothermal crystallization in the presence of alkali ions and quaternary ammonium compounds. Tetraalkylammonium salts, such as tetrapropylammonium bromide, are incorporated into the mixtures as templates to aid formation of the framework lattice.

The reported methods for producing crystalline gallosilicates, however, generally suffer from a variety of deficiencies which include: (1) use of large amounts of costly tetraalkylammonium salts which, during calcination of crude zeolite products, produce considerable amounts of pollutants and thus necessitate relatively expensive control equipment and (2) use of excessive reaction temperature which is in the range of 400° to 564° C. which is costly in terms of energy consumption. More important, gallosilicate crystals produced by the conventional methods have a highly variable particle size range which is an undesirable characteristic for their use as catalysts. The application of gallosilicates with a highly variable particle size in catalytic reactions which are controlled by the diffusion rates of products results in faster deactivation.

Furthermore, none of the reported methods produce crystalline gallosilicate having a silicon dioxide:gallium (III) oxide ratio equal or greater than 5. A lower silicon dioxide: gallium (III) oxide molar ratio, i.e. a higher proportion of gallium is desirable because the catalytic activity of the zeolite is directly proportional to the amount of gallium present in the lattice framework. As defined herein, catalytic activity is an inherent property of a zeolite catalyst to enhance the rate of conversion of low molecular weight hydrocarbons to higher aliphatics and aromatic compounds.

Accordingly, there is a substantial need in the field for improved methods for preparing crystalline gallosilicates which avoid at least one of the deficiencies mentioned above. Furthermore, there is an acute need in the art for gallosilicates with a silicon dioxide: gallium (III) oxide molar ratio equal or greater than 5.

SUMMARY OF THE INVENTION

The present invention relates to a method for preparing crystalline gallosilicates having a silicon dioxide: gallium (III) oxide molar ratio equal or greater than 5 and to the method of use thereof.

According to the method of the present invention, an aged, nuclei-forming gallosilicate gel having a molar ratio of silicon dioxide to gallium (III) oxide content greater than or equal to 5 is added to an alkaline solution containing solubleforms of silicates and gallates, e.g., amorphous silicon dioxide and gallium (III) salts, at a rate between about 2 and about 40% by weight of the mixture. The mixture is then reacted at a temperature between about 40° and 300° C. to form the crystalline gallosilicates of the present invention.

The method of the present invention utilizes reaction temperatures lower than the conventional methods of preparing crystalline gallosilicates and this represents an additional cost-savings in terms of reduced energy consumption. Moreover, little or no organic templates, e.g. quaternary ammonium compounds, are employed in the present inorganic method of preparing crystalline gallosilicates.

The proportion of gallium incorporated in the gallosilicate crystalline lattices of the present invention is clearly higher ($SiO_2/Ga_2O_3 \geq 40$ for gallosilicate crystals produced using the conventional methods and $SiO_2/Ga_2O_3 \geq 5$ for gallosilicate crystals produced with the method of the present invention). Hence the catalytic activity of the gallosilicates made according to the method of the present invention is enhanced as compared to the gallosilicate crystals made according to the prior art.

OBJECTS OF THE INVENTION

Accordingly, it is an object of the present invention to provide a simple, cost-effective method of preparing crystalline gallosilicates having a molar ratio of silicon dioxide to gallium (III) oxide equal or greater than 5 and having a more uniform particle size with enhanced catalytic activity.

It is another object of the invention to produce crystalline gallosilicates which are useful for the preparation of other catalysts and as absorbants.

It is a further object of the present invention to provide crystalline gallosilicates which can be employed in processes for converting low molecular weight hydrocarbons into higher aliphatics and aromatic compounds.

These and other objects of the present invention will be apparent in light of the detailed description of the invention set forth below.

DETAILED DESCRIPTION OF THE INVENTION

All literature references, patents and patent applications that are referred to in this specification are hereby incorporated by reference in their entirety.

The present invention involves a inorganic synthetic method for the preparation of crystalline gallosilicates having a silicon dioxide to gallium (III) oxide molar ratio equal or greater than 5. The invention is especially useful for producing gallosilicates suitable for use in industrial applications as catalysts and adsorbents, and displaying enhanced catalytic activity compared to prior art gallosilicates.

As defined herein, the term "nuclei-forming" is a property of substance which promotes crystallization by forming nucleation sites for crystal growth in supersaturated solutions. This promotion can be detected indirectly by evaluating the exponential number (n) in the Ciric-equation $[z=k\ t^n]$ describing the crystallization curve of the synthesis wherein $z$=crystallinity in %, k=factor of the nucleation velocity, and n=factor of the nucleation mechanism (See. for example, Ciric, J. (1968), J. Colloid Interface Sci., Vol. 28, 315–324).

According to the method of the present invention, a nuclei-forming, amorphous gallosilicate gel is prepared by mixing and reacting in a reaction vessel between about 20 gm and about 50 gm of silicon dioxide, preferably about 30 gm; between about 5 and about 10 gm sodium hydroxide, preferably about 9 gm; between about 5 and about 20 gm of an aqueous gallium trichloride solution; preferably about 10 gm, with between about 200 gm and about 500 gm water, preferably about 350 gm. The aqueous gallium trichloride solution has a specific weight (gm/ml) of between about 1.2 and about 1.5 gm, preferably about 1.38 gm, per ml and a gallium content of about 0.2 gm per ml of water.

The temperature of the reaction should be maintained at a temperature between about 15° and about 100° C., preferably about 90° C. The reaction mixture should be stirred (about 100 rpm) for a period between about 2 hours and about 100 days, preferably for a period of about 7 days.

A quaternary ammonium salt can be optionally added to the gel during mixing. Non-limiting examples of quaternary salts include tetraalkyl ammonium salts such as tetrapropylammonium bromide, tetrapropylammonium hydroxide, tetramethylammonium bromide and tetramethylammonium hydroxide. Preferred quaternary ammonium salts are tetrapropylammonium bromide and tetrapropylammonium hydroxide. The amount of quaternary ammonium salt that can be added is generally between about 0 gm and about 270 gm, preferably between about 0 gm and about 70 gm, such that a molar ratio of quaternary ammonium salt to silicon dioxide (between about 0 and about 2, preferably between about 0 and about 0.5) is maintained in the gel.

During this time period, formation of a gallosilicate gel occurs. The gel is then subjected to a decomposition or aging process at atmospheric pressure whereby the gel is kept at a constant temperature ranging between about 15° C. and about 100° C., preferably between about 20° C. and about 90° C. under constant stirring for a period between about 2 hours and about 100 days, preferably between about 2 and about 7 days.

The aged nuclei-forming gallosilicate gel contains a molar ratio of silicon dioxide to gallium (III) oxide greater than or equal to 5, a molar ratio of hydroxyl ions to silicon dioxide between about 0.05 and about 0.5, a molar ratio of quaternary ammonium compound to silicon dioxide between about 0 and about 2.0 and a molar ratio of water to silicon dioxide between about 10 and about 1000.

Thereafter, the aged gel is added to an aqueous, alkaline solution contained in a reaction vessel, preferably in an autoclave. Addition of the gel takes place under stirring (about 100 rpm) to form a mixture. The amount of aged gel is generally added to the alkaline solution is between about 2 and about 40% by weight of the mixture, preferably between about 5 and about 37%.

The alkaline solution contains between about 0.01 and about 0.04 moles of a gallium compound dissolved in dilute aqueous acid solution (e.g. about 12 ml); between about 0.1 and about 0.5 moles of alkali or alkali earth metal hydroxide, preferably between about 0.2 and about 0.3 moles; about 0.4 and 0.8 moles of a silicon compound, preferably between about 0.5 and about 0.7 moles, per liter of water contained in an autoclave.

Non-limiting examples of gallium compounds suitable for use in the alkali solution include gallium (III) oxide, gallium chloride, gallium hydroxide, gallium nitrate, gallium sulfate, alkali gallates and combinations of the foregoing. The preferred gallium compound is gallium (III) oxide which is readily formed by hydrolysis of gallium (III) chloride.

Non-limiting examples of silicon compounds suitable for use in the alkali solution include silicon dioxide, silicon hydroxide, silicon acetate, sodium water glass, alkali silicates and combinations of the foregoing. A preferred silicon compound is silicon dioxide.

Suitable acids for use in the invention include inorganic acids such as hydrochloric acid, sulfuric acid, and phosphoric acid. A preferred acid is hydrochloric acid. The molar concentration of the acid solution is generally between about 0.01 and about 8, preferably about 3.

Suitable metal hydroxides for use in the invention include sodium hydroxide, potassium hydroxide, calcium hydroxide, and lithium hydroxide. A preferred metal hydroxide is sodium hydroxide.

The mixture contains a molar ratio of silicon dioxide to gallium (III) oxide greater or equal to 5, a molar ratio of hydroxyl ions to silicon dioxide between about 0.05 and about 0.5, a molar ratio of a quaternary ammonium compound to silicon dioxide between about 0 and about 0.5, a molar ratio of water to silicon dioxide between about 20 and about 100, a molar ratio of alkali or alkali earth metal to silicon dioxide between about 0.3 and about 3.0.

A fluoride salt can be optionally added to the mixture as a synthesis stabilizer. Non-limiting examples of fluoride salts that are useful in this phase of the process include sodium fluoride and ammonium fluoride If fluoride is added to the mixture the molar ratio of fluoride salt to silicon dioxide should be maintained between about 0.4 and about 1.5, preferably between about 0.6 and about 1.0. That is, the amount of flouride added to the mixture should bring the ratio of flouride salt to silicon dioxide to within the range between about 0.4 and about 1.5.

Optionally, partially or totally crystalline gallosilicate seeding material can also be added to the mixture to increase the crystallization rate. The amount of seeding material that can be added is generally between about 0.1 and about 50%, preferably between about 1 and about 10% by weight of the total mixture.

During addition of the gel into the alkaline solution, the temperature of the resultant mixture should be maintained at a temperature between about 25° C. and about 100° C., preferably about 90° C. After addition of the aged nuclei-forming gel has been completed, the mixture is then subjected to crystallization conditions at autogenous pressure and at a constant temperature ranging between about 40° and about 300° C., preferably between about 100 and about 200° C. for a time period of between about 1 and about 72 hours, preferably between about 24 and about 48 hours. During this time the crystalline product precipitates out from the aqueous mixture.

The gallosilicates of the present invention can be crystallized in a single step at a constant temperature and within a predetermined time period or in a series of steps. For example, the mixture can be maintained at a different constant temperatures for various time periods, or at a plurality different temperatures for a different time period at each temperatures, but only within the aforementioned time and temperature ranges.

The crystalline gallosilicate is then separated from the mixture by conventional means, e.g., filtration, thoroughly washed with water to remove adhering impurities and dried at about 110° C. for about 12 hours. The general yields of gallosilicate crystals recovered is between about 20 and about 40 gm, usually about 30 gm.

The crystalline gallosilicates produced by the method of the present invention have a molar ratio of silicon dioxide to gallium (III) oxide greater or equal to 5. In contrast, the gallosilicate crystals produced using conventional techniques have a silicon dioxide/gallium III oxide molar ratio of 40 or greater. The particle size of the gallosilicate crystals of the invention is generally between about 3 and about 15 microns, usually about 10 microns. The catalytic activity of the gallosilicate crystals, measured as the conversion of propane to aromatic compounds at a temperature of about 500° C., at a reactor loading of about 2 $hr^{-1}$ and at atmospheric pressure, is generally of the order of between about 6% and about 25%, usually about 15%.

The working examples set forth below are intended to illustrate the invention without limiting its scope.

EXAMPLE 1 (Comparison Example)

In this example, gallosilicate crystals were synthesized in a conventional manner with the help of a template compound, tetrapropylammonium bromide. A homogenized reaction mixture, containing of 100 gm water, 6.07 gm $SiO_2$, 0.122 gm gallium metal (99.999% pure, Ingal Corporation, West Germany) dissolved in dilute HCl, 1.476 gm NaOH, 7.54 gm tetrapropylammonium bromide, and having the molar ratios of $H_2O/SiO_2=55$, $SiO_2/Ga_2O_3=125$, $OH^-/SiO_2=0.07$, tetrapropylammonium bromide-$/SiO_2=0.282$ is reacted for 96 hours at 160° C. in an autoclave under autogenous pressure.

After filtering, washing and drying at 110° C. for 12 hours, 4.5 gm of fully crystalline gallosilicates are obtained. The gallosilicates have the following chemical composition $124SiO_2 \cdot Ga_2O_3 \cdot 1.1 Na_2O$. This composition displays at least the interplanar spacings listed in Table 1 on X-ray diffraction. The particle size of the primary crystals range between 0.1 and 10 microns. When grown together, the crystals form agglomerates of between 5 and 20 microns. The catalytic activity of the crystals, measured as the conversion of propane to aromatic compounds at a temperature of 500° C., a reactor loading of 2 $h^{-1}$ and atmospheric pressure, is of the order of 4%.

TABLE 1

| (Gallosilicates Interplanar Spacings = Synthesized in Examples 1 to 4 herein) | |
|---|---|
| d = interplanar spacing (Angstroms) | Intensity (−) |
| 11.2 ± 0.2 | strong |
| 10.0 ± 0.2 | strong |
| 6.4 ± 0.1 | weak |
| 5.95 ± 0.1 | weak |
| 5.6 ± 0.1 | weak |
| 3.87 ± 0.05 | strong |
| 3.83 ± 0.05 | strong |
| 3.76 ± 0.05 | weak |
| 3.74 ± 0.05 | moderately weak |
| 3.66 ± 0.05 | weak |
| 2.01 ± 0.02 | weak |
| 1.99 ± 0.02 | weak |

EXAMPLE 2

36.687 gm of nuclei-forming gel are prepared by mixing 35.0 gm $H_2O$, 2.918 gm $SiO_2$, 0.057 gm $Ga_2O_3$, 0.385 gm NaOH, and 0.375 gm $GaCl_3$ aqueous solution having a density of 1.38 gm/mL and a gallium content of 0.2 gm per mL. The gel is aged for 7 days at 90° C.

This gel is mixed with a solution containing 4.997gm gallium metal dissolved in dilute HCl, 11.351 gm NaOH, 40.593 gm $SiO_2$ (RW filler) in 1 liter of water in an autoclave and homogenized. The reaction mixture with the molar ratios of: $H_2O/SiO_2=83$, $SiO_2/Ga_2O_3=126$, $OH^-/SiO_2=0.375$ is reacted under autogenous pressure for six hours at 140° C., for a further six hours at 165° C. and then for 1.5 days at 180° C. under hydrothermic condition.

After filtration, washing and drying at 110° C. for 12 hours, about 50 gm of a completely crystalline gallosilicate with the chemical composition of $98SiO_2 \cdot Ga_2O_3 \cdot 1.1Na_2O$ are obtained. These crystals have the interplanar spacings listed in Table 1. The particle size of the gallosilicate crystals is between about 3 and 5 microns. The catalytic activity, measured as the conversion of propane to aromatic compounds at a temperature of 500° C., a reactor loading of $2h^{-1}$ and atmospheric pressure is of the order of 6%.

EXAMPLE 3

40.210 gm of a nuclei-forming gel, aged for seven days at 90° C. and having the following molar composition: $H_2/SiO_2=55$, $SiO_2/Ga_2O_3=60$, $OH^-/SiO_2=0.07$, tetrapropylammonium bromide$/SiO_2=0.141$ is added to a homogenized reaction batch consisting of 65 gm water, 2.047 gm SiO$_2$, 0.079 gm gallium metal dissolved in dilute HCl and 1.827 gm NaOH.

This reaction mixture having molar ratios of H$_2$O/SiO$_2$=80, SiO$_2$/Ga$_2$O$_3$=60, OH$^-$/SiO$_2$=0.45, tetrapropylammonium bromide/SiO$_2$=0.07, is reacted for 48 hours at 180° C. under autogenous pressure. After filtration, washing and drying at 110° C. for 12 hours, about 4.5 gm of a completely crystalline gallosilicate having the chemical composition of 51SiO$_2$·Ga$_2$O$_3$·1.1Na$_2$O is obtained. This composition has the interplanar spacings listed in Table 1 above. The particle size of gallosilicate crystals is between about 3 and 5 microns. The catalytic activity, measured as the conversion of propane to aromatic compounds at a temperature of 500° C., a reactor loading of 2 h$^{-1}$ and atmospheric pressure is of the order of 15%.

EXAMPLE 4

0 9.9960 gm of a nuclei-forming gel, aged for three days at 90° and having the following molar composition: H$_2$/SiO$_2$=55, SiO$_2$/Ga$_2$O$_3$=50, OH$^-$/SiO$_2$=0.07, tetrapropylammonium bromide/SiO$_2$=0.141 is added to a homogenized reaction batch consisting of 65 gm water, 2.047 gm SiO$_2$, 1.1 gm gallium solution, 1.424 gm sodium hydroxide. This reaction batch with the molar ratios of H$_2$/SiO$_2$=80, SiO$_2$/Ga$_2$O$_3$=30, OH$_-$$^-$/SiO$_2$−0.45, tetrapropylammonium bromide/SiO$_2$=0.09, is reacted for 24 hours at 180° C. under autogenous pressure. After filtration, washing and drying at 110° C. for 12 hours, a completely crystalline gallosilicate with the chemical composition of 26SiO$_2$·Ga$_2$O$_3$·1.1Na$_2$O is obtained. This crystalline composition has the interplanar spacings listed in Table 1. The particle size of the gallosilicate crystals is between about 3 and 5 microns. The catalytic activity, measured as the conversion of propane to aromatic compounds at a temperature of 500° C., a reactor loading of 2 h$^{-1}$ and atmospheric pressure is of the order of 25%.

What is claimed is:

1. A method for preparing a crystalline gallosilicate having a formula of:

wherein M represents a metal cation with a valency of n and x ranges between 0 and 10, said method comprising the steps of:
   (a) mixing an aged, amorphous gallosilicate nuclei-forming gel having a Si$_2$O/Ga$_2$O$_3$ molar ratio greater than or equal to 5 with an aqueous alkaline solution having a Si$_2$O/Ga$_2$O$_3$ molar ratio greater than or equal to 5;
   (b) reacting said mixture at a temperature ranging between about 40° and about 300° C. to produce said crystalline gallosilicate; and
   (c) separating said crystalline gallosilicate from said mixture.

2. The method according to claim 1 wherein said gel comprises a molar ratio of silicon dioxide to gallium (III) oxide greater or equal to 5, a molar ratio of hydroxyl ions to silicon dioxide ranging between about 0.01 to about 1.0, a molar ratio of a quaternary ammonium compound to silicon dioxide ranging between about 0 to about 2.0 and a molar ratio of water to silicon dioxide ranging between about 10 to about 1000.

3. The method according to claim 1 wherein said gel comprises a molar ratio of silicon dioxide to gallium (III) oxide ranging between about 10 and about 200, a molar ratio of hydroxyl ions to silicon dioxide ranging between about 0.05 and about 0.5, a molar ratio of tetrapropylammonium hydroxide to silicon dioxide ranging between about 0 and about 0.5 and a molar ratio of water to silicon dioxide ranging between about 20 and about 100.

4. The method according to claim 1 wherein said alkaline solution comprises a silicon compound and a gallium compound.

5. The method according to claim 1 wherein said crystalline gallosilicate has a Si/Ga ratio ranging between about 5 and about 100.

6. The method according to claim 4 wherein said silicon compound comprises silicon dioxide, silicon hydroxide, silicon acetate sodium water glass, alkali silicates or combinations of the foregoing.

7. The method according to claim 4 wherein said gallium compound comprises gallium metal, gallium oxide, gallium nitrate, gallium sulfate, gallium hydroxides, alkali gallates or combinations of the foregoing.

8. The method according to claim 4 further comprising adding a quaternary ammonium compound to said solution.

9. The method according to claim 8 wherein said quaternary ammonium compound comprises tetrapropylammonium bromide, tetrapropylammonium hydroxide, tetramethylammonium bromide, or tetramethylammonium hydroxide.

10. The method according to claim 1 wherein said mixture comprises a molar ratio of silicon dioxide to gallium (III) oxide greater or equal to 5, a molar ratio of hydroxyl ions to silicon dioxide ranging between about 0.05 and about 0.5, a molar ratio of a quaternary ammonium compound to silicon dioxide ranging between about 0 and about 0.5, a molar ratio of water to silicon dioxide ranging between about 20 and about 100, and a molar ratio of alkali or alkali earth metal to silicon dioxide ranging between about 0.3 and about 3.0.

11. The method according to claim 1 comprising aging said gel at atmospheric pressure at a temperature ranging between about 15 and about 100° C. for a time period ranging between about 2 hours and about 100 days.

12. The method according to claim 1 comprising aging said gel at atmospheric pressure at a temperature ranging between about 20° to about 90° C. for a time period ranging between about 2 to about 7 days.

13. The method according to claim 1 comprising adding said gel to said solution in an amount ranging between about 2 and about 40% by weight of said mixture.

14. The method according to claim 1 comprising adding said gel to said solution in an amount ranging between about 5 and about 37% by weight of said mixture.

15. The method according to claim 1 comprising aging said gel at atmospheric pressure at a temperature ranging between about 20° to about 90° C. for a time period ranging between about 2 and about 7 days.

16. The method according to claim 1 comprising reacting said mixture for a time period ranging between about 1h and about 72h.

17. The method according to claim 3 comprising reacting said mixture for a time period ranging between about 24 and about 48h.

18. The method according to claim 1 further comprising adding a fluoride salt to said mixture in a molar ratio of fluoride to silicon dioxide ranging between about 0.4 and about 1.5.

19. The method according to claim 17 wherein said fluoride salt comprises sodium fluoride or ammonium fluoride.

20. The method according to claim 1 further comprising adding a crystalline gallosilicate to said mixture in an amount ranging between about 0.1 and about 50% by weight of said mixture.

21. A catalyst comprising a gallosilicate prepared in accordance to claim 1.

22. A crystalline gallosilicate comprising the following chemical formula:

$$(M^{n+})_{x/n}[(GaO_2)_x(SiO_2)_{96-x}\pi.$$

wherein M represents a metal cation with a valency of n and x ranges between 0 and 10, said gallosilicate having a silicon dioxide to gallium (III) oxide molar ratio greater or equal to 5.

23. A method for preparing a crystalline gallosilicate having a formula of:

$$(M^{n+})_{x/n}[(GaO_2)_x(SiO_2)_{96-x}]$$

wherein M represents a metal cation with a valency of n and x ranges between 0 and 10, said method comprising the steps of:

(a) mixing an aged, amorphous gallosilicate nuclei-forming gel having a $Si_2O/Ga_2O_3$ molar ratio greater than or equal to 5, an aqueous alkaline solution having a $Si_2O/Ga_2O_3$ molar ratio greater than or equal to 5, and fluoride salt in a molar ratio of fluoride to silicon dioxide ranging between about 0.4 and about 1.5 to form a mixture;

(b) reacting said mixture at a temperature ranging between about 40° and about 300° C. to produce said crystalline gallosilicate; and (c) separating said crystalline gallosilicate from said mixture.

24. The method according to claim 23, wherein said fluoride salt comprises sodium fluoride or ammonium fluoride.

* * * * *